United States Patent [19]
Chan

[11] Patent Number: 6,099,759
[45] Date of Patent: Aug. 8, 2000

[54] 2-ADAMANTYL BENZOPYRANS, THE COMPOSITIONS AND (CO)POLYMER MATRICES CONTAINING THEM

[75] Inventor: You-Ping Chan, Lyons, France

[73] Assignee: Corning Incorporated, Corning, N.Y.

[21] Appl. No.: 09/217,741

[22] Filed: Dec. 21, 1998

Related U.S. Application Data

[62] Division of application No. 08/984,278, Dec. 3, 1997, Pat. No. 5,888,432.
[60] Provisional application No. 60/038,357, Feb. 13, 1997.

[30] Foreign Application Priority Data

Dec. 23, 1996 [FR] France .................................. 96 15850

[51] Int. Cl.$^7$ .............................. G02B 5/23; C08F 24/00; C08F 269/00; C08G 63/91; C08G 65/04
[52] U.S. Cl. .......................... 252/586; 525/165; 525/178; 525/191; 525/203; 525/206; 525/242; 525/54.21; 525/54.23; 525/279; 525/284; 525/326.1; 525/326.7; 525/326.8; 525/327.2; 525/327.3; 525/403; 525/404; 525/409; 525/410; 525/411; 525/412; 525/413; 528/420; 528/421; 526/268

[58] Field of Search ............................. 252/586; 523/106; 525/284, 279, 54.21, 54.23, 165, 178, 191, 203, 206, 242, 326.1, 326.7, 326.8, 327.2, 327.3, 403, 404, 409, 410, 411, 412, 413; 526/268; 528/421, 420

[56] References Cited

FOREIGN PATENT DOCUMENTS 6-192651  7/1994  Japan .
7-145371  6/1995  Japan .

*Primary Examiner*—Philip Tucker
*Attorney, Agent, or Firm*—Angela N. Nwaneri; Peter Rogalskyj

[57] ABSTRACT

The present invention has for subjects, novel benzopyran derivatives, substituted in position 2 with an adamantyl group as well as the compositions and (co)polymer matrices containing such derivatives. Said derivatives possess interesting photochromic properties.

15 Claims, No Drawings

2-ADAMANTYL BENZOPYRANS, THE COMPOSITIONS AND (CO)POLYMER MATRICES CONTAINING THEM

This application is a division of U.S. patent application Ser. No. 08/984,278, filed Dec. 3, 1997, which issued as U.S. Pat. No. 5,888,432 on Mar. 30, 1999, and which claims priority from French Patent Application No. 96 15850, filed Dec. 23, 1996, and from Provisional U.S. Patent Application Ser. No. 60/038,357, filed Feb. 13, 1997.

The present invention relates to novel compounds of the 2-adamantyl benzopyran type, which possess, in particular, photochromic properties. It relates also to photochromic, compositions and photochromic ophthalmic articles (for example lenses) containing said novel compounds.

The photochromic compounds are able to change color under the influence of a poly- or monochromatic light (for example UV) and to regain their initial color when the light irradiation ceases, or under the influence of a poly- or monochromatic light different from the first, or under the influence of temperature and/or of poly- or monochromatic light different from the first.

The photochromic compounds find applications in various fields, for example for the manufacture of ophthalmic lenses, contact lenses, solar protection lenses, filters, camera optical systems or photographic apparatus optical systems or optical systems of other optical devices, and observation optical systems, glazings, decorative objects, bill elements or even for the storage of information by optical inscription (coding).

In the field of ophthalmic optics, and in particular in the spectacles trade, a photochromic lens, comprising one or more photochromic compounds, must possess:

a high transmission in the absence of ultraviolets, a low transmission (high colorability) under solar irradiation, adapted coloration and discoloration kinetics, a tint acceptable to the consumer (gray or brown, preferably) with, preferably, a maintenance of the chosen tint during coloration and discoloration of the lens, a maintenance of the performances, i.e. the properties in a temperature range of 0–40° C., an important durability, since these desired objectives are sophisticated corrective lenses and are therefore expensive.

These lens characteristics are, in fact, determined by the active photochromic compounds that it contains; these compounds must in addition be perfectly compatible with the organic or inorganic support making up the lens.

It is in other respects to be noted that obtaining a gray or brown tint may necessitate the use of at least two photochromes of different colors, i.e. having distinct maximal absorption wavelengths in the visible. This association further imposes other requirements of the photochromic compounds. In particular, the coloration and discoloration kinetics of the (two or more) associated active photochromic compounds must be roughly identical. The same applies for their stability with time and, also, the same applies for their compatibility with a plastic or inorganic support.

Among the numerous photochromic compounds described in the prior art, benzopyrans or naphthopyrans described in the patents U.S. Pat. No. 3,567,605, U.S. Pat. No. 3,627,690, U.S. Pat. No. 4,818,096, U.S. Pat. No. 4,826,977, U.S. Pat. No. 5,200,116, U.S. Pat. No. 5,238,981, U.S. Pat. No. 5,458,814 and in the Research Disclosure No. 36144, may be cited, which are of the following formula:

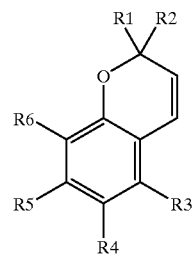

These compounds claim to satisfy the specifications defined above. In reality, if these compounds really have one or more of the basic properties sought after, such as a high transmission in the absence of ultraviolets and a high colorability under solar irradiation, all the compounds described hitherto have not the complete combination of properties sought after which are necessary for the production of satisfactory articles which can be manufactured industrially.

It is to the credit of the Applicant to have found, in a surprising way, that the presence of an adamantyl group in position 2 of naphtho- or benzopyrans allowed lowering the λmax of the colored form. This type of molecules, novel per se, adapts well in association with blue and/or violet and/or red complementary photochromes in order to give gray or brown tints.

The present application thus has, for first subject, benzopyran derivatives which are substituted in position 2 with an adamantyl group, itself optionally substituted with at least one linear or branched alkyl group which comprises from 1 to 6 carbon atoms. Advantageously, said adamantyl group is linked in position 1.

The carbon in position 2 of said benzopyran derivatives (the carbon which carries therefore the adamantyl group and advantageously the adamant-1-yl group) is an asymmetric carbon. The derivatives of the invention are therefore generally in the form of racemic mixtures. Nevertheless, the pure isomers of said derivatives also make up an integral part of the present invention.

In the context of a preferred variant of the invention, said carbon, in position 2, in addition to said adamantyl group, bears a second substituent group S (≠hydrogen). Said 2-adamantyl-2-S benzopyrans have particularly interesting photochromic properties.

In the context of its first subject, such as defined above, the present invention relates to benzopyran derivatives, of the following formula (I)

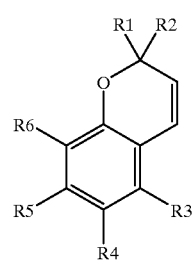

in which

R1 is an adamantyl group, optionally substituted with at least one linear or branched alkyl group which comprises from 1 to 6 carbon atoms; said adamantyl group being preferably linked in position 1 (preferably:

R1 = 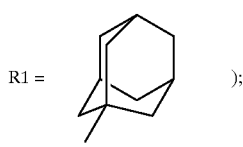;

R₂ is:
  a linear or branched alkyl group which comprises from 1 to 12 carbon atoms;
  a cycloalkyl group which comprises from 3 to 12 carbon atoms;
  an aryl or heteroaryl group which comprises in its basic structure either 6 to 24 carbon atoms or 4 to 24 carbon atoms together with at least one heteroatom selected from sulfur, oxygen and nitrogen; said basic structure being optionally substituted with at least one substituent selected from:
    a halogen and notably fluorine, chlorine and bromine;
    a linear or branched alkyl group which comprises from 1 to 6 carbon atoms;
    a linear or branched alkoxy group which comprises from 1 to 6 carbon atoms;
    a linear or branched haloalkyl or haloalkoxy group which comprises from 1 to 6 carbon atoms, and notably a fluoroalkyl group of this type;
    an —NH₂ group;
    an —NHR group, R representing a linear or branched alkyl group which comprises from 1 to 6 carbon atoms;
    a group

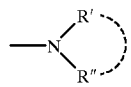

R' and R", identical or different, representing independently a linear or branched alkyl group which comprises from 1 to 6 carbon atoms, or representing, together with the nitrogen atom to which they are linked, a 5 to 7 membered ring which can include at least one other heteroatom selected from oxygen, sulfur and nitrogen, said nitrogen being optionally substituted with an R''' group, a linear or branched alkyl group comprising from 1 to 6 carbon atoms;
    an aralkyl or heteroaralkyl group, the alkyl group, linear or branched, comprising from 1 to 4 carbon atoms and the aryl and heteroaryl groups having the definitions given above; said aralkyl group consisting advantageously of a phenyl (C₁–C₄)alkyl group;
R₃ to R₆, identical or different, are, independently:
  hydrogen;
  a halogen and notably fluorine, chlorine or bromine;
  a linear or branched alkyl group which comprises from 1 to 12 carbon atoms;
  a cycloalkyl group which comprises from 3 to 12 carbon atoms;
  a linear or branched alkoxy group, which comprises from 1 to 12 carbon atoms;
  a haloalkyl, halocycloalkyl, haloalkoxy group corresponding respectively to the alkyl, cycloalkyl, alkoxy groups above, substituted with at least one halogen atom, notably selected from fluorine, chlorine and bromine;
  an aryl or heteroaryl group having the same definition as that given above for R₂;
  an aralkyl or heteroaralkyl group, the alkyl group, linear or branched comprising from 1 to 4 carbon atoms, and the groups aryl and heteroaryl having the same definitions as those given above for R₂;
  an amine or amide group: —NH₂, —NHR, —CONH₂, —CONHR,

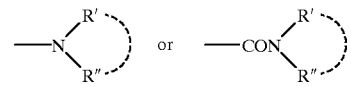

R, R', R" having respectively their definitions given above for the amine substituents of the meaning R₂: aryl or heteroaryl;

a —OCOR₇ or —COOR₇ group, R₇ representing a straight or branched alkyl group comprising from 1 to 6 carbon atoms, or a cycloalkyl group comprising from 3 to 6 carbon atoms, or a phenyl group optionally substituted with at least one of the substituents listed above for the meaning of R₂: aryl or heteroaryl, or
  at least two of the groups R₃, R₄, R₅, R₆ are optionally annelated in order to constitute a radical of the phenyl, naphthyl, pyridyl, benzopyridyl, furyl, benzofuryl, indene or indole type; said radical being optionally substituted with one or more groups, identical or different, having the definitions given above for R₃ to R₆ ; the non-annelated groups being such as defined above.

Among said derivatives of formula (I) above, preferred are those which are of formula (I) in which R2 is an aryl or heteroaryl group whose basic structure is selected from those of the phenyl, naphthyl, biphenyl, pyridyl, furyl, benzofuryl, dibenzofuryl, N-(C₁–C₆)alkylcarbazole, thienyl, benzothienyl, dibenzothienyl groups.

Particularly preferred compounds of the invention are of the following formulae (I1) and (I2):

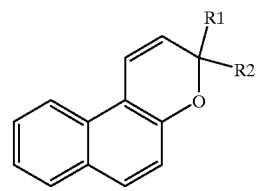
(I1)

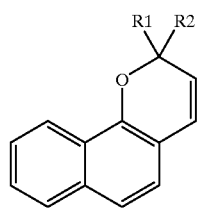
(I2)

in which:

R1 is an adamant-1-yl group,

R2 is a phenyl group optionally substituted with at least one alkyl, alkoxy, dialkylamine group of formula

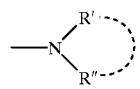

; said alkyl, alkoxy, dialkylamine substituent groups being such as defined above as $R_2$ substituents, aryl or heteroaryl;

the naphthyl group is optionally substituted with at least one group of one of the definitions given above for $R_3$ to $R_6$.

Among the substituents of the benzopyran derivatives of the invention, notably of those of formulae I, I1 and I2 above, some of them do exist which comprise and/or form at least one polymerizable and/or cross-linkable reactive group. The presence of such reactive groups can turn out to be opportune. Thus, the present invention includes in its first subject, the class of the benzopyran derivatives substituted in position 2 by an adamantyl group and whose structure includes at least one group reactive towards polymerization and/or cross-linking; said group being notably able to consist of an alkenyl group, advantageously of the vinyl or allyl type, a methacryloyl, an acryloyl or an epoxy group.

Thus, the compounds of the invention which belong to said class, may be apprehended as monomers, of a different nature or not, which are able to react with themselves or with other comonomers in order to form homopolymers and/or copolymers, which bear a photochromic functionality (insofar as said monomers of the invention bear said photochromic functionality) and which possess mechanical properties of macromolecules.

It follows that another subject of the present invention is formed by these homopolymers or copolymers, linear or branched, which are at least in part constituted by benzopyran derivatives of the invention.

Along the same lines, the abovementioned benzopyran derivatives can be envisaged to be cross-linking agents having reactive functions which are able to allow bridging between polymer chains of photochromic nature or not. The reticulates, which are able to be so obtained, also constitute another subject of the present invention.

The preparation of the benzopyran derivatives according to the invention do not present any particular difficulties. Said derivatives can be obtained, in a general manner, by condensation of a phenol, having a hydrogen in position 2 and being optionally substituted in position(s) 3, 4, 5 and/or 6, with a propargylic alcohol derivative, substituted in position 1 by an adamantyl group optionally substituted with at least one linear or branched alkyl group which comprises from 1 to 6 carbon atoms and optionally substituted with another substituent.

This synthetic route is classical and has been described in the prior art references cited above. This synthetic route, for the compounds of the invention which are of formula I in which R1=adamant-1-yl, is schematically thus:

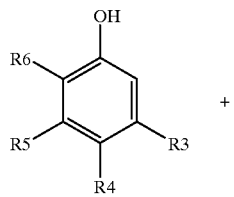

-continued

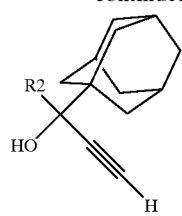

The condensation reaction can be carried out in solvents such as toluene and tetrahydrofuran, in the presence of an acid catalyst such as sulfonic acid, chloroacetic acid or acidic alumina.

It is to the credit of the Applicant to have prepared and tested the original benzopyran derivatives described above; said derivatives possessing particularly advantageous photochromic properties. More specifically, these novel compounds are endowed with a high colorability, with λ.max values lower than the known analogous compounds: benzopyran derivatives having two aryl groups in position 2.

These compounds are, in other respects, compatible with support matrices of organic polymer or of inorganic material, both in the form included in the matrix and in the form of a coating.

In solution or in a polymer matrix, the compounds according to the invention are colorless or slightly colored in the initial state and rapidly develop an intense coloration under a UV light (365 nm) or a light source of the solar type. Finally, they regain their initial color once the irradiation ceases.

According to another of its subjects, the present invention relates to the use of said compounds of the invention as photochromic agents. In other terms, the Applicant hereby proposes:

novel photochromic compounds, which consist of the benzopyran derivatives such as defined above, taken separately or in a mixture with themselves and/or with at least one other photochromic compound of another type and/or with at least one non-photochromic colorant;

novel photochromic compositions, which comprise at least one benzopyran derivative such as defined above and/or at least one (co)polymer and/or reticulate including in its structure at least one of said benzopyran derivatives of the invention. Such photochromic compositions can include at least one other photochromic compound of another type and/or at least one non-photochromic colorant and/or at least one stabilizer.

Said photochromic compounds of another type, non-photochromic colorants, stabilizers are prior art products known to the person skilled in the art.

In the context of the present invention, the associations of photochromic compounds of the invention, and/or associations of photochromic compounds of the invention and photochromic compounds of another type according to prior art, are particularly recommended, if they are convenient for generating gray or brown tints.

The compounds of the invention, notably as photochromic compounds, can be used in solution. Thus, a photochromic solution can be obtained by solubilizing the compound in an organic solvent such as toluene, dichloromethane, tetrahydrofuran or ethanol. The solutions obtained are generally colorless and transparent. Once exposed to solar light, they develop a high coloration and regain the colorless state once they are placed in a zone of less exposure to solar rays or, in other terms, when they are no longer submitted to UV. It is sufficient, in general, for a very low concentration of product (in the order of 0.01 to 5% by weight) to obtain an intense coloration.

The compounds of the invention can also be used as a photochromic material uniformly dispersed in the mass or in the surface of a polymer matrix. In fact, the most interesting applications of the compounds of the invention are those in which the photochrome is dispersed uniformly within or on the surface of a polymer, a copolymer or a mixture of polymers. The (co)polymer matrix which comprises said photochrome of the invention (at least one, in the free form, in the form of a (co)polymer and/or reticulate, and/or in the form of a photochromic composition, such as defined above) constitutes another subject of the present invention.

The implementation processes which can be envisaged for obtaining such a matrix are very varied. Among those known to the person skilled in the art, it can be cited, for example, the diffusion in the (co)polymer, from a suspension or solution of the photochrome, in a silicone oil, in an aliphatic or aromatic hydrocarbon, in a glycol, or from another polymer matrix. The diffusion is commonly carried out at a temperature of 50 to 200° C. for a period of time of 15 minutes to some hours, according to the nature of the polymer matrix. Another implementation technique consists in mixing the photochrome in a formulation of polymerizable materials, depositing this mixture on a surface or in a mould and then carrying out the copolymerization. These implementation techniques and others are described in the article by Crano et al. "Spiroxazines and their use in photochromic lenses" published in Applied Photochromic Polymer Systems, Ed. Blackie and Son Ltd—1992.

In accordance with a variant of this subject of the invention, it is also possible to envisage grafting the photochromes on (co)polymers. Thus, the invention also relates to the (co)polymers grafted with at least one of the photochromes described hereinbefore. The expression "(co) polymer matrix comprising at least one photochrome of the invention" means therefore both matrices which comprise said photochrome in their masses and in their sufaces, and matrices grafted with said photochrome.

As examples of polymer materials preferred for optical applications of the photochromic compounds according to the invention, the following products can be mentioned:

an alkyl, cycloalkyl, aryl or (mono, di, tri or tetra) arylalkyl polyacrylate or polymethacrylate optionally halogenated or comprising at least one ether and/or ester and/or carbonate and/or carbamate and/or thiocarbamate and/or urea and/or amide group, a polystyrene, polyether, polyester, polycarbonate (e.g. polycarbonate of bisphenol-A, polycarbonate of diallyl diethylene glycol), polycarbamate, polyepoxy, polyurea, polyurethane, polythiourethane, polysiloxane, polyacrylonitrile, polyamide, aliphatic or aromatic polyester, vinylic polymer, cellulose acetate, cellulose triacetate, cellulose acetate-propionate or a polyvinylbutyral, a copolymer of two or more types of monomer or mixtures of polymers referred to above, preferably a polycarbonate-polyurethane, poly(meth)acrylate-polyurethane, polystyrene-poly(meth)acrylate or even a polystyrene-polyacrylonitrile, advantageously a mixture of a polyester and a polycarbonate or a poly(meth) acrylate.

The amount of photochrome used in the (co)polymer matrix depends on the degree of darkening desired. In a customary manner, an amount of it is used which is between 0.001 and 20% by weight. The photochromic compounds according to the invention can be used alone or in a mixture with other products in order to form a composition which can be presented in solid or liquid form, for example in solution or in dispersion, as has already been indicated above. These compositions, which constitute a subject of the invention as already indicated above, can therefore comprise the compounds of the invention and other complementary photochromic compounds which allow obtaining dark colorations, for example gray or brown, desired by the public in applications such as the solar or ophthalmic spectacles trade. These complementary photochromic compounds can be those known to the person skilled in the art and described in the literature, for example chromenes (U.S. Pat. No. 3,567,605, U.S. Pat. No. 5,238,981, WO-A-94 22 850, EP-A-562 915), spiropyrans or naphthospiropyrans (U.S. Pat. No. 5,238,981) and spiroxazines (Crano et al., "Applied Photochromic Polymer Systems", Ed. Blackie & Son Ltd, 1992, chapter 2).

Said compositions according to the invention can also comprise:

non-photochromic colorants which allow adjusting the tint, and/or one or more stabilizers, like for example an antioxidant, and/or one or more anti-UV agents, and/or one or more anti-radical agents, and/or one or more photochemical excited states deactivators.

These additives can notably allow the improvement of the durability of said compositions.

According to another of its aspects relative to the application of the compounds of the invention, the present invention has also for subject ophthalmic articles, such as the articles of the solar or ophthalmic spectacles trade, comprising at least one compound according to the invention and/or at least one (co)polymer and/or reticulate, formed, at least in part, from compounds of the invention and notably recurrent units of the (I), (I1) and (I2) type and/or at least one composition comprising the compounds of the invention and notably those of formulae (I), (I1) and (I2), according to the invention, such as defined above, and/or at least one matrix, such as defined above, of an organic polymer material or inorganic material or even of an organic-inorganic hybrid material incorporating therein at least one compound of the invention.

In practice, the articles which are most particularly aimed at by the present invention are the photochromic solar or ophthalmic lenses, glazings (panes for buildings, for locomotive engines, automobiles), optical devices, decorative articles, solar protection articles, information storages, . . . .

The present invention is illustrated by the following examples of synthesis and of photochromic validation of compounds of the invention (benzopyran derivatives substituted in position 2 with an adamantyl group).

EXAMPLES

Synthesis and Properties of Photochromic Compounds 1 to 4 of the Invention

Example 1

Synthesis of Compound (1)

Step 1: Phenyl adamantyl ketone is synthesized by the reaction of adamantane acid chloride and phenyl magnesium bromide in THF at 0° C. The yield after purification is 41%.

Step 2: 1-Adamantyl-1-phenyl-propargylic alcohol is obtained by the reaction of lithium acetylide (diamine complex) with phenyl adamantyl ketone in DMSO followed by hydrolysis and extraction with toluene. The yield is 90%.

Step 3: The compound obtained in Step 2 (3.2 g) is reacted with 6-methoxy-2-naphthol (1.74 g) in 30 ml of toluene in the presence of a catalytic amount of para-toluenesulfonic acid under reflux for 1 hour. The medium is then neutralized with 0.5 g of sodium bicarbonate, then chomatographed on a silica gel column using toluene as eluent. The product is then recrystallized in a mixture of methanol/diisopropylether. 300 mg of compound (1) (see Table 1 hereinafter) are thus obtained in the form of a white powder. The $^1$H NMR confirms the structure of the product. In solution in THF, the color of the solution changes from colorless to yellow in the sun and looses its color rapidly in the shade.

Example 2

Synthesis of Compound (2)

Compound 2 (see Table 2 hereinafter) is obtained in an analogous way to that used for compound 1 from 4.2 g of 1-adamantyl-1-phenyl-propargylic alcohol and 2,3 g of 1-naphthol. The two reagents are held under reflux in xylene and in the presence of a catalytic amount of para-toluenesulfonic acid for 15 minutes. The product is then isolated by chromatography on a silica gel column with a yield of 11%.

Examples 3 and 4

Synthesis of Compounds (3) and (4) of the Invention and of Those of the Comparative Examples C1 to C3

The compounds 3 and 4 (see Table 2 hereinafter) and those of the comparative examples C1 to C3 (see Tables 1 and 2 hereinafter) have been synthesized in an analogous way from corresponding synthons and then isolated by chromatography on silica and/or by recrystallizations.

Example 5

Incorporation of the Compounds in a Polyacrylate

General procedure: 5 mg of each-of the compounds are solubilized in 10 g of tetraethoxyl bisphenol A dimethacrylate (marketed under the name of Diacryl 121 by the Akzo Company) containing also 40 mg of 2,2'-azobis(2-methylbutyronitrile). The solution is then degassed, regassed with argon, and poured into a glass lens mold of 8 cm in diameter and 2 mm thickness. The mold is then placed in an oven at 70° C. for 12 hours. After turning out, a rigid and transparent lens is obtained. Under irradiation of the solar type, the glass rapidly develops an intense violet coloration and becomes colorless again in the shade. The photochromic characteristics are given in Tables 1 and 2 hereinafter. By way of comparison, the characteristics of the compounds of analogous structure of the prior art are given in said Tables 1 and 2 hereinafter. After 15 minutes' exposure to a Xenon lamp, the UV-visible spectrum is recorded and the λmax of the principal visible band is measured.

TABLE 1

Compounds derived from 2-naphthol

| COMPOUND | STRUCTURE | λmax |
|---|---|---|
| 1 | 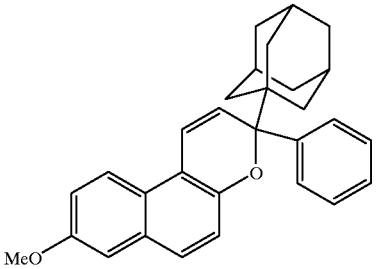 | 436 nm |
| C1 (US-A-5,238,981) | 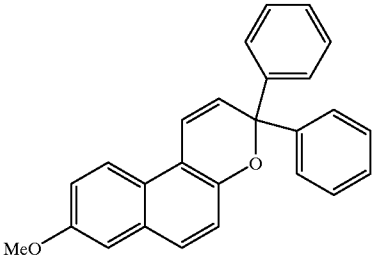 | 473 nm |

TABLE 2

Compounds derived from 1-naphthol

| compound | structure | λmax |
|---|---|---|
| 2 | 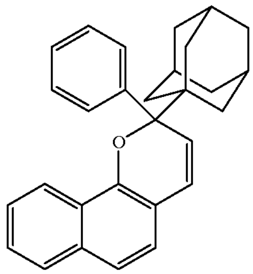 | 440 nm |
| 3 | 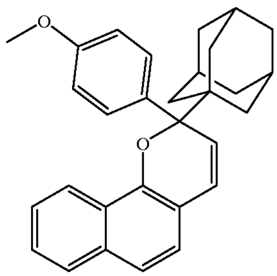 | 444 nm |
| 4 | 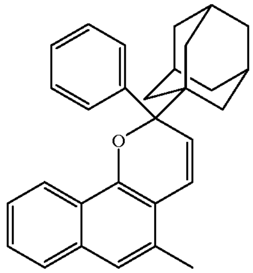 | 452 nm |
| C2 (RD 36144) | 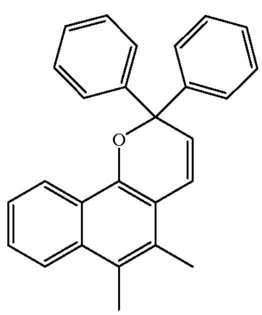 | 475 nm |
| C3 (US-A-5,200,116) | 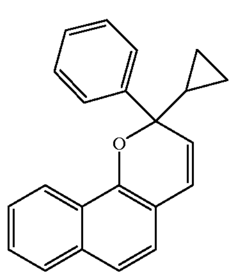 | 465 nm |

It is demonstrated by these examples that the presence of the adamantyl group in the place of a phenyl group allows lowering the λmax of the photochrome. Moreover, we observe discoloration kinetics which are a little slower for the compounds of the invention. These molecules therefore adapt well in association with the blue and/or violet and/or red complementary photochromes of equivalent discoloration kinetics for obtaining gray or brown tints.

What is claimed is:

1. (Co)polymer obtained by polymerizing at least one monomer constituted of at least one benzopyran derivative, optionally in the presence of at least one other monomer, wherein said at least one benzopyran derivative is characterized by having a structure selected from the group consisting of:

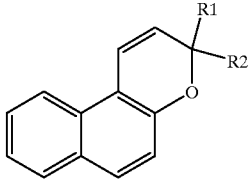

(I1)

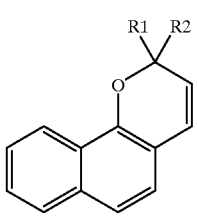

(I2)

in which $R_1$ is an adamant-1-yl group; and $R_2$ is a phenyl group substituted with at least one alkyl, alkoxy, or dialkylamine group

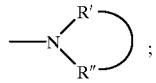

where R' and R" can be the same or different and represent independently a linear or branched alkyl group which comprises from 1 to 6 carbon atoms or represent, together with the nitrogen atom to which they are linked, a 5 to 7 membered ring which can include at least one other heteroatom selected from oxygen, sulfur, and nitrogen;

and wherein said benzopyran derivative is further characterized in that said benzopyran derivative includes at least one group reactive towards polymerization, said reactive group being selected from the group consisting of alkenyl, methacryloyl, acryloyl, and epoxy groups.

2. (Co)polymer matrix, characterized in that it comprises:
   at least one copolymer according to claim 1; and
   at least one other (co)polymer.

3. (Co)polymer matrix according to claim 1, characterized in that the at least one other (co)polymer is selected from the group consisting of:
   alkyl, cycloalkyl, aryl, (mono, di, tri, or tetra) aralkyl polyacrylate or polymethacrylate, polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, polyvinylbutyral, and mixtures thereof.

4. (Co)polymer according to claim 1, wherein the at least one other monomer is selected from the group consisting of vinyl monomers, allyl monomers, methacroyl monomers, acroyl monomers, epoxy monomers, and combinations thereof.

5. (Co)polymer according to claim 1, wherein the at least one other monomer is a monomer whose polymerization product is a polymer selected from the group consisting of a polyacrylate, polymethacrylate, polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, polyvinylbutyral, and mixtures thereof.

6. Ophthalmic or solar article comprising at least one (co)polymer according to claim 1.

7. Ophthalmic or solar article according to claim 6, characterized in that it is constituted by a lens.

8. Glazing or optical device comprising at least one (co)polymer according to claim 1.

9. Reticulate obtained by reacting at least one cross-linking agent constituted of at least one benzopyran derivative with polymer chains bearing reactive groups capable of reacting with said at least one cross-linking agent, wherein said at least one benzopyran derivative is characterized by having a structure selected from the group consisting of:

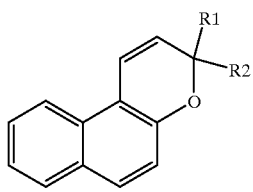

(I1)

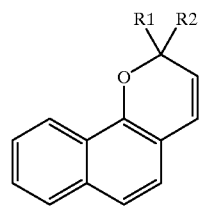

(I2)

in which $R_1$ is an adamant-1-yl group; and $R_2$ is a phenyl group substituted with at least one alkyl, alkoxy, or dialkylamine group

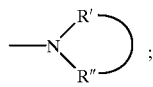

where R' and R" can be the same or different, and represent independently a linear or branched alkyl group which comprises from 1 to 6 carbon atoms, or represent, together with the nitrogen atom to which they are linked, a 5 to 7 membered ring which can include at least one other heteroatom selected from oxygen, sulfur, and nitrogen;

and wherein said benzopyran derivative is further characterized in that said benzopyran derivative includes one or more reactive functions capable of reacting with said polymer chains' reactive groups and bridging between said polymer chains, said one or more reactive functions being selected from the group consisting of alkenyl groups, methacryloyl groups, acryloyl groups, epoxy groups, and combinations thereof.

10. (Co)polymer matrix, characterized in that it comprises:

at least one reticulate according to claim 9; and at least one (co)polymer.

11. (Co)polymer matrix according to claim 10, characterized in that the at least one (co)polymer is selected from the group consisting of:

alkyl, cycloalkyl, aryl, (mono, di, tri, or tetra) aralkyl polyacrylate or polymethacrylate, polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, polyvinylbutyral, and mixtures thereof.

12. Reticulate according to claim 9, wherein the polymer chains' reactive groups are selected from the group consisting of vinyl groups, allyl groups, methacroyl groups, acroyl groups, epoxy groups, and combinations thereof.

13. Ophthalmic or solar article comprising at least one reticulate according to claim 9.

14. Ophthalmic or solar article according to claim 13, characterized in that it is constituted by a lens.

15. Glazing or optical device comprising at least one reticulate according to claim 9.

* * * * *